(12) United States Patent
Cheshire et al.

(10) Patent No.: US 6,265,409 B1
(45) Date of Patent: *Jul. 24, 2001

(54) PYRIDINE DERIVATIVES AND PHARMACEUTICAL COMPOSITIONS CONTAINING THEM

(75) Inventors: David Cheshire, Chilwell; David Cladingboel, Mountsorrel; Simon Hirst, West Bridgford; Carol Manners, Arnold; Michael Stocks, Long Eaton, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/068,520

(22) PCT Filed: Mar. 10, 1998

(86) PCT No.: PCT/SE98/00423

§ 371 Date: May 11, 1998

§ 102(e) Date: May 11, 1998

(87) PCT Pub. No.: WO98/42669

PCT Pub. Date: Oct. 1, 1998

(30) Foreign Application Priority Data

Mar. 25, 1997 (SE) .................................... 9701098
Jun. 9, 1997 (SE) .................................... 9702197

(51) Int. Cl.$^7$ ...................... C07D 401/12; A61K 31/496
(52) U.S. Cl. .......................... 514/255; 514/277; 514/357; 546/339; 546/332; 546/340; 544/360
(58) Field of Search .................................... 546/339, 332, 546/340; 514/277, 357, 255; 544/360

(56) References Cited

U.S. PATENT DOCUMENTS 5,977,105 * 11/1999 Cheshire et al. ..................... 514/241

* cited by examiner

Primary Examiner—Jane Fan
(74) Attorney, Agent, or Firm—Nixon & Vanderhye

(57) ABSTRACT

The invention relates to novel pyridyl derivatives, their use as medicaments, pharmaceutical formulations including them and methods for their preparation.

5 Claims, No Drawings

PYRIDINE DERIVATIVES AND PHARMACEUTICAL COMPOSITIONS CONTAINING THEM

This invention relates to novel pyridyl derivatives, their use as medicaments, pharmaceutical formulations including them and methods for their preparation.

European Patent Applications EP-A-0 264 114 and EP-A-0 267 439 disclose certain phenylalkyl- and phenylalkoxypyridine alkanol derivatives and their use as platelet-activating factor (PAF) antagonists.

A series of structurally distinct compounds have now been found to be useful for the modulation of inflammatory conditions. In a first aspect the present invention therefore provides a compound of formula I:

(I)

wherein;
X is $(CH_2)_nO$, $(CH_2)_nS$ or $CH_2CH_2$;
n is 1 or 2;
$Ar^1$ is naphthyl or biphenyl substituted by one or more groups selected from bromo, iodo, —Y—$NR^1C(O)NR^2$—$R^3$, —O—Z—$C(O)NR^2R^3$, —O—Z—$C(S)NR^2R^3$, —Y—$C(O)NR^2R^3$, —Y—$SO_2NR^2R^3$, —Y—$NR^2R^3$, —Y—$C(S)NR^2R^3$, —Y—$C(O)R^4$, —Y—$OC(O)R^4$, —Z—$CH_2$—$OR^4$, —Y—$CO_2R^4$, —Y—$NR^5C(O)NR^6$—Z—$R^7$, —$SO_2NR^5C(O)NR^2R^3$, —Y—$C(O)NR^6$—Z—$R^7$, —Y—$C(S)NR^6$—Z—$R^7$, —Y—$N(R^5)SO_2R^6$, —Y—$N(R^5)C(O)R^6$ or —Y—$N(R^5)CO_2R^6$; where:
Y is a bond, $C_{1-6}$ alkylene or $C_{2-6}$ alkenylene;
$R^2$ and $R^3$ are independently hydrogen or $C_{1-6}$ alkyl or together with the nitrogen atom to which they are attached form an optionally substituted 5- to 7-membered heterocyclic ring optionally containing a further heteroatom selected from nitrogen, oxygen or sulfur;
$R^1$, $R^4$, $R^5$ and $R^6$ are independently hydrogen or $C_{1-10}$ alkyl (optionally substituted by one or more fluorine atoms);
Z is $C_{1-6}$ alkylene; and
$R^7$ is a group $NR^5C(O)R^6$, $NR^5CO_2R^6$, $NR^2R^3$, $CO_2R^8$ or $OR^9$, where $R^2$, $R^3$, $R^5$ and $R^6$ are as defined above, $R^8$ is hydrogen, $C_{1-6}$ alkyl, $C_{1-6}$ alkylaryl or aryl optionally substituted by hydroxy, and $R^9$ is hydrogen or $C_{1-6}$ alkyl, or a salt or solvate thereof,
provided that:
$Ar^1$ is not naphthyl substituted by O—Z—$C(O)NR^2R^3$ or $C(O)R^4$, and
$Ar^1$ is not biphenyl substituted by —$SO_2NR^2R^3$, —$NR^2R^3$, $SO_2NR^2R^3$, —$C(O)R^4$, —$OC(O)R^4$, —$CO_2R^4$, $N(R^5)SO_2R^6$ or —$N(R^5)C(O)R^6$ Alkyl and alkenylene groups, whether alone or part of another group, can be straight chained or branched.

Suitably X is $(CH_2)_nO$, $(CH_2)_nS$ or $CH_2CH_2$. Preferably X is $CH_2O$, $CH_2S$ or $CH_2CH_2$. More preferably X is $CH_2O$.

Suitably $Ar^1$ is naphthyl or biphenyl substituted by one or more groups selected from bromo, iodo, —Y—$NR^1C(O)NR^2$—$R^3$, —O—Z—$C(O)NR^2R^3$, —O—Z—$C(S)NR^2R^3$, —Y—$C(O)NR^2R^3$, —Y—$SO_2NR^2R^3$, —Y—$NR^2R^3$, —Y—$C(S)NR^2R^3$, —Y—$C(O)R^4$, —Y—$OC(O)R^4$, —Z—$CH_2$—$OR^4$, —Y—$CO_2R^4$, —Y—$NR^5C(O)NR^6$—Z—$R^7$, —$SO_2NR^5C(O)NR^2R^3$, —Y—$C(O)NR^6$—Z—$R^7$, —Y—$C(S)NR^6$—Z—$R^7$, —Y—$N(R^5)SO_2R^6$, —Y—$N(R^5)C(O)R^6$ or —Y—$N(R^5)CO_2R^6$. Preferably Y is $C_{1-6}$ alkylene or $C_{1-6}$ alkenylene. The substituent(s) can be present on any suitable position on the naphthyl and biphenyl groups.

Preferably $Ar^1$ is naphthyl or biphenyl substituted by one or more groups selected from bromo, —Y—$C(O)OR^4$, —Y—$C(O)NR^2R^3$, Y—Z—$NR^2R^3$, —Y—$NR^1C(O)NR^2R^3$, —Y—$NR^5C(O)NR^6$—Z—$R^7$, or —Y—$C(O)NR^6$—Z—$R^7$ where Y is CH=CH, $CH_2CH_2$. Preferably one substituent is present.

When $Ar^1$ is naphthyl or biphenyl substituted by —Y—$C(O)OR^4$ preferably $R^4$ is hydrogen or $C_{1-4}$ alkyl, in particular methyl.

When $Ar^1$ is naphthyl or biphenyl substituted by —Y—$C(O)NR^2R^3$, $R^2$ and $R^3$ are independently hydrogen or $C_{1-6}$ alkyl or together with the nitrogen atom to which they are attached form an optionally substituted 5- to 7-membered heterocyclic ring optionally containing a further heteroatom selected from nitrogen, oxygen or sulfur. Examples of such rings include piperazine, pyrrolidine and morpholine groups. Suitable optional substituents for such rings include $C_{1-6}$alkyl and $CO_2C_{1-6}$ alkyl. Preferably one of $R^2$ or $R^3$ is hydrogen and the other is $C_{1-4}$ alkyl, in particular methyl, or $R^2$ and $R^3$ are both $C_{1-4}$ alkyl, in particular methyl or $R^2$ and $R^3$ form a morpholine ring or a piperazine ring optionally substituted by $C_{1-6}$alkyl in particular methyl, or $CO_2C_{1-6}$ alkyl, in particular $CO_2Me$ and $CO_2t$-butyl groups.

When $Ar^1$ is naphthyl or biphenyl substituted by —Y—$NR^1CONR^2R^3$, $R^1$ and $R^2$ are preferably hydrogen and $R^3$ is preferably $C_{1-6}$alkyl, in particular methyl.

When $Ar^1$ is naphthyl or biphenyl substituted by —Y—$C(O)NR^6$—Z—$R^7$, $R^6$ is preferably hydrogen. $R^7$ is suitably a group $NR^5C(O)R^6$, $NR^5CO_2R^6$, $CO_2R^8$ or $OR^9$ where $R^5$ and $R^6$ are independently hydrogen or $C_{1-6}$ alkyl and $R^8$ is hydrogen, $C_{1-6}$ alkyl, $C_{1-6}$ alkylaryl or aryl. When $R^7$ is $NR^5C(O)R^6$ or $NR^6CO_2R^6$, $R^5$ is preferably hydrogen and $R^6$ is preferably $C_{1-6}$alkyl. Preferably $R^7$ is $CO_2R^8$ or $OR^9$. When $R^7$ is $CO_2R^8$ suitable aryl groups include phenyl, preferably $R^8$ is hydrogen or benzyl.

Particularly preferred compounds of the invention include:
(2R)-1-[2-(6-Bromonaphthyloxy)]-4-(3-pyridyl)-2-butanol,
(2R)-1-[2-(6-(3-trans-Propenoic acid, methyl ester)naphthyloxy)]-4-(3-pyridyl)-2-butanol,
(2R)-1-[2-(6-(3-Propanoic acid, methyl ester)naphthyloxy)]-4-(3-pyridyl)-2-butanol,
(2R)-1-[2-(6-(3-(N-methyl)propanamide)naphthyloxy]-4-(3-pyridyl)-2-butanol,
(2R)-1-[2-(6-(3-trans-Propenoic acid)naphthyloxy)]-4-(3-pyridyl)-2-butanol,
(2R)-1-[2-(6-(3-(N-methyl)propenamide)naphthyloxy]-4-(3-pyridyl)-2-butanol,
(2R)-1-[2-(6-(3-(N,N-Dimethyl)propenamide)naphthyloxy]-4-(3-pyridyl)-2-butanol,
(2R)-1-[2-(6-(3-(N,N-Dimethyl)propanamide)naphthyloxy-]-4-(3-pyridyl)-2-butanol,
(2R)-1-[2-(6-(3-propanoic acid)naphthyloxy)]-4-(3-pyridyl)-2-butanol,
(2R)-1-[2-(6-(3-N-(benzyloxycarbonylmethyl)propanamide)naphthyloxy]-4-(3-pyridyl)-2-butanol,
(2R)-1-[2-(6-(3-N-(Ethanoic acid)propanamide)naphthyloxy]-4-(3-pyridyl)-2-butanol,
(2R)-1-[2-(6-(3-(N-Acetylpiperazino)-1-oxopropyl)naphthyloxy]-4-(3-pyridyl)-2-butanol,
(2R)-1-[2-(6-(3-(4-Morpholinyl)-1-oxopropyl)naphthyloxy]-4-(3-pyridyl)-2-butanol, (2R)-1-[2-(6-(3-N-(2-Hydroxyethyl)propanamide) naphthyloxy]-4-(3-pyridyl)-2-butanol,
(2R)-1-[2-(6-(3-(4-(4-(1,1-Dimethylethoxycarbonyl)) piperazine)-1-oxopropyl)naphthyloxy]-4-(3-pyridyl)-2-butanol,
(2R)-1-[2-(6-(3-(N-(Hexahydro-1,4-diazine)-1-oxopropyl) naphthyloxy]-4-(3-pyridyl)-2-butanol,
(2R)-1-[2-(6-(3-(N,N-Dimethyl)propanamide) naphthyloxy]-4-(3-pyridyl)-2-butanol,
(2S)-1-[2-(6-Bromonaphthyloxy)]-4-(3-pyridyl)-2-butanol,
(2S)-1-[2-(6-(3-(N,N-Dimethyl)propenamide) naphthyloxy]-4-(3-pyridyl)-2-butanol,
(2S)-1-[2-(6-(3-(N,N-Dimethyl)propanamide) naphthyloxy]-4-(3-pyridyl)-2-butanol,
(2R)-1-[3'-(N,N-Dimethylphenylacetamide)-4-biphenyl-4-yloxy]-4-(3-pyridyl)-2-butanol,
(2R)-1-[2-(6-(3-(N-6-(1,1-Dimethylethylcarbamoyl)hexyl) propanamide)naphthyl-oxy]-4-(3-pyridyl)-2-butanol,
or a salt or solvate thereof.

Compounds of the invention can form pharmaceutically acceptable solvates and salts. The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic acids. Compounds of the invention may also form alkali metal salts such as magnesium, sodium, potassium and calcium salts.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

According to the invention there is also provided a process for the preparation of compounds of formula I as hereinbefore defined which comprises:

(a) for compounds of formula (I) where X is $CH_2O$, reaction of a compound of formula (II):

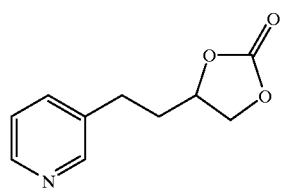

(II)

with a compound of formula (III):

(III)

in which $Ar^1$ is as defined in formula (I), and optionally thereafter:
removing any protecting groups,
converting the compound of formula (I) into a further compound of formula (I)
forming a pharmaceutically acceptable salt.

Reaction of compounds of formulae (II) and (III) can be carried out the presence of a suitable base in an inert solvent at elevated temperature, for example using cesium carbonate in dimethylformamide at about 100° C.

Compounds of formula (II) can be prepared by treating compounds of formula (IV):

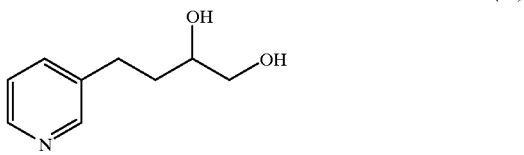

(IV)

with 1,1'-carbonyldiimidazole. The reaction can be carried out in a solvent such as chloroform at elevated temperature, preferably at reflux temperature.

Compounds of formula (I) can be converted into further compounds of formula (I) using standard procedures. For example compounds of formula (I) where $Ar^1$ is naphthyl substituted by bromo can be converted to compounds of formula (I) where $Ar^1$ is naphthyl substituted by —CH=CH—C(O)OR$^4$, —CH=CH—C(O)NR$^2$R$^3$ (i.e. where Y is CH=CH) by reacting with compounds of formula (V) or (VI) respectively:

(V)

(VI)

in which $R^1$, $R^2$ and $R^3$ are as defined in formula (I) using Heck chemistry. For example compounds of formula (I) where $Ar^1$ is naphthyl substituted by bromo or iodo can be treated with a palladium catalyst and a compound of formula (V) or (VI) in a suitable solvent at elevated temperature. If desired the palladium catalyst can be formed in situ.

The resulting compounds of formula (I) prepared using the above chemistry can be converted into yet further compounds of formula (I) by reduction of the double bond of the —CH=CH—C(O)OR$^4$ or —CH=CH—C(O)NR$^2$R$^3$ group. This can be carried out under standard hydrogenation conditions, for example using palladium on charcoal.

Other procedures for converting compounds of formula (I) into further compounds of formula (I) will be apparent to those skilled in the art. For example compounds of formula (I) containing a —Y—C(O)OR$^1$ group where $R^1$ is methyl can be converted to compounds of formula (I) having a —Y—C(O)NHMe group by treating with methylamine in methanol at elevated temperature. Preferably the reaction is carried out at about 100° C. in a sealed vessel. The same transformation can be carried out using trimethylaluminium and methylamine hydrochloride in toluene at reduced temperature, e.g. at about 0° C.

Compounds of formula (I) containing a —Y—C(O)OR$^1$ group can also be converted to the corresponding carboxylic acids by hydrolysis. Preferred conditions include treatment with lithium hydroxide in a suitable solvent system, for example in water/THF at ambient temperature.

Compounds of formula (I) containing a —Y—C(O)OH group can also be converted to compounds of formula (I) having a —Y—C(O)NR$^2$R$^3$ group by reacting with the appropriate amine. For example amines of formula HNR$^2$R$^3$ can be reacted in a suitable solvent such as dimethylformamide in the presence of 1-hydroxybenzotriazole and 1-ethyl-3-(3'-dimethylaminopropyl)-carbodiimide.

Compounds of formula (I) containing a —Y—C(O)NR$^2$R$^3$ group can be converted to compounds of formula (I) having a —Y—NR$^2$R$^3$ group by treating with borane-tetrahydrofuran complex.

Other procedures for the preparation of compounds of formula (I) include:

(b) preparation of compounds of formula (I) where X is $CH_2S$, $CH_2O$ or $(CH_2)_2$ by reaction of (±)-3-(2-oxiranylethyl)pyridine or α-(chloromethyl)-3-pyridinepropanol either with a compound of formula (VII):

$$MYAr^1 \qquad (VII)$$

where Y is O, S or $CH_2$, M is Li, Na, K or MgHal where Hal is halogen and $Ar^1$ is as defined in formula (I), for example at ambient or reduced temperature in a suitable solvent such as dimethylformamide or tetrahydrofuran; or with a compound of formula (VIII):

$$HYAr^1 \qquad (VIII)$$

where Y is as defined in formula (VIII) in the presence of a base such as sodium hydroxide in a suitable solvent such as aqueous ethanol, or (c) preparation of compounds of formula (I) where $Ar^1$ is a substituted biphenyl group by reaction of a compound of formula (IX):

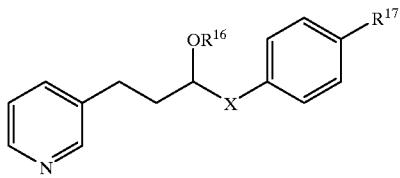

(IX)

with a compound of formula (X):

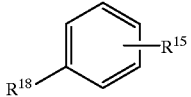

(X)

where X is as defined above, $R^{15}$ is the $Ar^1$ substituent and $R^{16}$ is a suitable hydroxy protecting group, and one of $R^{17}/R^{18}$ is triflate or halo and the other is $B(OH)_2$, or ZnHal under the conditions of the Suzuki reaction (*Synthetic Communications* 11(7), 513–519, 1081) for example at about 100° C. in the presence of a suitable catalyst and base (e.g. tetrakis(triphenylphosphine)palladium (0) and aqueous sodium carbonate) in a suitable solvent (e.g. ethanol/toluene).

After procedures (b), and (c) compounds can be deprotected, interconverted and salts prepared as described above.

Suitable $R^{16}$ is a hydroxy protecting group, for example t-butyldimethylsilyl.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

Novel intermediates form a further aspect of the invention.

Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques.

The compounds of the invention are useful because they possess pharmacological activity and more particularly activity in the modulation of inflammatory and allergic conditions, for example as shown in the test described below. The compounds of the invention inhibit the activation of a range of cell types from haematopoetic lineage, including mast cells, neutrophils and eosinophils. In a further aspect the invention therefore provides a compound of formula (I) or a pharmaceutically acceptable salt or solvate thereof for use in therapy.

The compounds of the invention are indicated for use in the treatment or prevention of allergic, inflammatory, auto-immune, proliferative and hyper-proliferative diseases.

The compounds of the invention are also indicated in the treatment and prevention of allergic, inflammatory or auto-immune conditions of the lung, including reversible obstructive airways diseases which includes asthma (e.g. bronchial, allergic, intrinsic asthma, extrinsic and chronic asthma), and associated manifestations of the disease (late responses, hyper-responsiveness), also farmer's lung and related diseases, fibrosis, ideopathic interstitial pneumonia, chronic obstructive airways disease (COPD), bronchiectasis, cystic fibrosis, eosinophilic pneumonias, adult respiratory distress syndrome (ARDS), emphysema and alveolitis, for example cryptogenic fibrosing alveolitis.

Further, the compounds of the invention are indicated in the treatment or prevention of allergic, inflammatory or auto-immune conditions in the nose including all conditions characterised by inflammation of the nasal mucous membrane such as acute rhinitis, allergic rhinitis, atrophic rhinitis, chronic rhinitis including rhinitis caseosa, hypertrophic rhinitis, rhinitis purulenta and rhinitis sicca, rhinitis medicamentosa, membranous rhinitis including croupous, fibrinous and pseudomembranous rhinitis, scrofulous rhinitis, seasonal rhinitis including rhinitis nervosa (hay fever) and vasomotor rhinitis. Of particular interest are allergic rhinitis and seasonal rhinitis including rhinitis nervosa (hay fever). The compounds are also indicated for the treatment of nasal polyps and allergic manifestations of the nasopharynx other than those described hereintofore.

The compounds of the invention are also indicated the treatment or prevention of allergic, inflammatory or auto-immune conditions of the eye such as conjunctivitis (allergic, acute, vernal, of hay fever, chronic), inflammation disorders of the eyelids, cornea, uveal tract and retina.

The compounds of the invention are also indicated in the treatment and prevention of allergic, inflammatory and auto-immune conditions of the gastrointestinal tract such as food allergy and food intolerance, ulcerative colitis, Crohn's disease, irritable bowel disease, gastric ulcers, and food related allergic diseases which have symptomatic manifestations remote from the gastrointestinal tract, for example migraine, rhinitis and eczema.

The compounds of the invention are indicated for use in the treatment or prevention of allergic, inflammatory or auto-immune conditions of the skin such as psoriasis, atopical dermatitis, contact dermatitis/dermatitis herpetiformis, erythema nodosum, urticaria, cutaneous eosinophilias, acne, Alopecia areata, eosinophilic fascitis dermatomyositis, photoallergic sensitivity and periodontal disease.

The compounds of the invention are therefore indicated for use in the treatment or prevention of allergic, inflammatory or auto-immune conditions of the joints and connective tissue, including osteoarthritis, rheumatoid arthritis, systemic lupus erythematosis, vasculitis, Wegener's granulomatosis, polyarthritis nodosa, bursitis, tendonitis, gout, Behcet's syndrome, ankylosing sponditis, Reiter's syndrome and psoriatic arthritis.

The compounds of the invention are indicated in the treatment and prevention of allergic, inflammatory, and auto-immune conditions of the circulatory system including atheroma, reperfusion injury (e.g. on angioplasty), myocardial infarction, thrombosis and vascular and tissue damage caused by ischaemic disease or injury.

The compounds of the invention are indicated in the treatment and prevention of allergic, inflammatory or auto-immune conditions of the CNS including Parkinson's disease, Alzheimers and other dementias, stroke and subarachnoid haemorrhage. The compounds of the invention are indicated in the treatment and prevention of inflammatory conditions of the liver for example hepatitis, cirrhosis and glomerulonephritis.

The compounds of the invention are indicated in the treatment and prevention of allergic, inflammatory or auto-immune conditions of the bladder and uro-genital tract including cystitis.

The compounds of the invention are indicated in the treatment and prevention of tumours and other proliferative diseases.

Of particular interest amongst the above indications is use of the compounds of the invention in a reversible obstructive airways disease, most particularly asthma and especially the treatment and prophylaxis of asthma and rhinitis.

According to a further aspect of the invention there is thus provided the use of a compound of formula I, as hereinbefore defined, or a pharmaceutically acceptable salt or solvate thereof in the manufacture of a medicament for the treatment of the above diseases, in particular reversible obstructive airways disease, especially the treatment and prophylaxis of asthma.

Administration of the compounds of the invention may be topical (for example by inhalation to the lung). The compounds of the invention may be inhaled as a dry powder which may be pressurised or non-pressurised.

In non-pressurised powder compositions, the active ingredient in finely divided form may be used in admixture with a larger sized pharmaceutically acceptable inert carrier.

The composition may alternatively be pressurised and contain a compressed gas, e.g. nitrogen, or a liquefied gas propellant. In such pressurised compositions, the active ingredient is preferably finely divided. The pressurised composition may also contain a surface active agent. The pressurised compositions may be made by conventional methods. The compounds of the invention may be administered systemically (for example by oral administration to the gastrointestinal tract). The active ingredient may be formulated together with known adjuvants, diluents or carriers using conventional techniques to produce tablets or capsules for oral administration to the gastrointestinal tract.

Examples of suitable adjuvants, diluents or carriers for oral administration in the form of tablets, capsules and dragees include microcrystalline cellulose, calcium phosphate, diatomaceous earth, a sugar such as lactose, dextrose or mannitol, talc, stearic acid, starch, sodium bicarbonate and/or gelatin.

According to a further aspect of the invention there is provided a pharmaceutical composition including a compound of formula I or a salt or solvate thereof as hereinbefore defined in association with a pharmaceutically acceptable adjuvant, diluent or carrier.

Suitable doses for such oral administration are in the range from 0.3 to 30 mg $kg^{-1}$ $day^{-1}$, for example 3 mg $kg^{-1}$ $day^{-}$.

According to a further aspect of the present invention, there is provided a method of treatment or prophylaxis of a reversible obstructive airways disease, in particular asthma, which method comprises administration of a therapeutically effective amount of a compound of formula I as hereinbefore defined, or a pharmaceutically acceptable derivative thereof, to a person suffering from, or susceptible to, the disease.

It will be understood by those skilled in the art that certain functional groups in the compounds of the invention may be protected using appropriate protecting groups as hereinbefore described to form "protected derivatives" of compounds of the invention. It will also be appreciated that, although such protected derivatives may not possess pharmacological activity as such, they may be administered and thereafter metabolised in the body to form compounds of the invention which are pharmacologically active. Such derivatives may therefore be described as "prodrugs". All protected derivatives and prodrugs of compounds of formula I are included within the scope of the invention.

The invention is illustrated by the following Examples.

EXAMPLE 1

(2R)-1-[2-(6-Bromonaphthyloxy)]-4-(3-pyridyl)-2-butanol a) (2R, 3E/Z)-4-(3-Pyridyl)-1,2-O-isopropylidenebut-3-en-1,2-diol A solution of n-butyllithium (2.5 M in hexanes; 100.8 ml) was added dropwise to a stirred suspension of 3-pyridylmethyltriphenylphosphonium chloride hydrochloride (53.39 g, *J. Med. Chem.* 1986, 29, 1461) in tetrahydrofuran (50 ml) at −40° C. The resulting mixture was stirred at room temperature for 30 minutes and was then cooled to −70° C. A solution of 2,3-O-(S)-isopropylidene-L-glyceraldehyde (15.2 g) (ex Oxford Asymmetry; see *Organic Synthesis* (1995) 72, 1) in tetrahydrofuran (10 ml) was added. The resulting mixture was stirred and allowed to reach room temperature over 3 hours. The mixture was poured into brine (500 ml) and extracted into ethyl acetate. The combined extracts were dried over anhydrous magnesium sulfate, filtered and concentrated under reduced pressure. The residue was purified by column chromatography over silica eluting with diethyl ether to give the sub-title compound as an oil (21.2 g).

MS (EI) 205 (M)$^+$ $^1$H NMR (CDCl$_3$) major Z-diastereomer 8.53(2H, d); 7.61(1H, dt); 7.29(1H, dd); 6.67(1H, d); 5.85(1H, dd); 4.83(1H, q); 4.16(1H, t); 3.71(1H, t); 1.49(3H, s); 1.39(3H, s).

b) (2R)-4-(3-Pyridyl)-1,2-O-isopropylidenebutane-1,2-diol

A solution of (2R, 3E/Z)-4-(3-pyridyl)-1,2-O-isopropylidenebut-3-en-1,2-diol (21.2 g, Example 1a)) in ethyl acetate (200 ml) was hydrogenated for 2 hours at 3 atmospheres pressure using palladium on carbon (10%, 0.5 g) as catalyst. The reaction was filtered through celite® and the residue washed with ethyl acetate. The combined filtrate and washings were concentrated under reduced pressure and the residue obtained purified by column chromatography over silica eluting with diethyl ether to give the sub-title compound as an oil (20.5 g).

MS (ESI) 208 (M+H)$^+$ $^1$H NMR (CDCl$_3$) 8.48–8.45(2H, m); 7.52(1H, dt); 7.23 (1H, dd); 4.10(1H, quintet); 4.04(1H, t); 3.55(1H, t); 2.84–2.64(2H, m); 1.94–1.80(2H, m); 1.44(3H, s); 1.36(3H, s).

c) (2R)-4-(3-Pyridyl)-1,2-butanediol (2R)-4-(3-Pyridyl)-1,2-O-isopropylidenebutane-1,2-diol (20.4 g, Example 1b)) was dissolved in hydrochloric acid (2M, 100 ml) and was stirred for 40 minutes. The mixture was neutralised with saturated aqueous sodium hydrogencarbonate solution and was concentrated under reduced pressure. The residue obtained was triturated with ethyl acetate and filtered. The residue was washed with ethyl acetate and the combined organic extracts were dried over anhydrous magnesium sulfate, filtered and concentrated under reduced pressure. The residue obtained was purified by column chromatography over silica eluting with ethyl acetate:methanol (9:1) to give the sub-title compound as an oil (16.4 g).

MS (APCI) 168 (M+H)$^+$ $^1$H NMR (CDCl$_3$) 8.44–8.40(2H, m); 7.54(1H, d); 7.22 (1H, dd); 3.73–3.67(1H, m); 3.65(1H, dd); 3.48(1H, dd); 2.90–2.70(2H, bm); 2.87–2.68(2H, m); 1.84–1.67(2H, m).

d) (4R)-4-[2-(3-Pyridyl)ethyl]-1,3-dioxin-2-one

A solution of (2R)-4-(3-pyridyl)-1,2-butanediol (0.42 g, Example 1c)) and 1,1'-carbonyldiimidazole (0.49 g) in chloroform (15 ml) was heated at reflux for 20 minutes. The reaction was cooled and concentrated under reduced pressure. The residue was purified by column chromatography over silica eluting with methanol:dichloromethane (1:19) to give the sub-title compound as an oil (0.35 g).

MS (APCI) 194 (M+H)$^+$ $^1$H NMR (CDCl$_3$) 8.52–8.49(2H, m); 7.53(1H, d); 7.26 (1H, dd); 4.73–4.66(1H, m); 4.54 (1H, dd); 4.09 (1H, dd); 2.94–2.88 (1H, m); 2.86–2.72 (1H, m); 2.17–2.09 (1H, m); 2.02–1.97 (1H, m).

e) (2R)-1-[2-(6-Bromonaphthyloxy)]-4-(3-pyridyl)-2-butanol

Cesium carbonate (1.69 g) and 6-bromo-2-naphthol (1.16 g) were added to a solution of (4R)-4-[2-(3-pyridyl)ethyl]-1,3-dioxin-2-one (1.2 g, Example 1d)) in dry dimethylformamide (30 ml) and heated at 100° C. for 16 hours. After cooling, the reaction mixture was poured into water and extracted with ethyl acetate. The combined extracts were washed with brine, dried over anhydrous magnesium sulfate, filtered and concentrated under reduced pressure. The residue was purified by column chromatography over silica eluting with acetone:isohexane (1:1) to give the title compound as a white solid (1.0 g).

m.p. 119–120° C.

MS (APCI) 374 (M+H)$^+$ $^1$H NMR (CDCl$_3$) 8.53(1H, d); 8.47(1H, dd); 7.91(1H, d); 7.65(1H, d); 7.56–7.59(2H, m); 7.49–7.51(1H, m); 7.22–7.25(1H, m); 7.16(1H, dd); 7.08(1H, dd); 4.06–4.09 (2H, m); 3.95–4.0(1H, m); 2.90–2.94(1H, m); 2.81–2.85 (1H, m); 2.59(1H, s); 1.89–1.98(2H, m).

EXAMPLE 2

(2R)-1-[2-(6-(3trans-Propenoic acid, methyl ester)naphthyloxy)]-4-(3-pyridyl)-2-butanol Palladium(II) acetate (0.06 g), tri-o-tolylphosphine (0.16 g), methyl acrylate (2.42 ml) and triethylamine (4 ml) were added to a solution of (2R)-1-[2-(6-bromonaphthyloxy)]-4-(3-pyridyl)-2-butanol (1.0 g, Example 1e)) in acetonitrile (20 ml) and the mixture heated in a sealed tube at 70° C. for 11 hours. The solvents were removed under reduced pressure and the residue purified by column chromatography over silica eluting with isohexane:acetone (1:1) to give the title compound as a pale yellow solid (0.91 g).

m.p. 121.5–124° C.

MS (APCI) 378 (M+H)$^+$ $^1$H NMR (CDCl$_3$) 8.43(1H, d); 8.35(1H, dd); 8.08(1H, s); 7.81–7.77(3H, m); 7.72(1H, d, J=17 Hz); 7.61(1H, d); 7.31(1H, d); 7.28–7.25(1H, m); 7.25–7.15(1H, m); 6.65(1H, d, J=17 Hz); 5.07(1H, d); 3.98(2H, d); 3.83–3.77(1H, m); 3.69(3H, s); 2.79–2.74(1H, m); 2.69–2.63(1H, m); 1.86–1.82(1H, m); 1.73–1.71(1H, m).

EXAMPLE 3

(2R)-1-[2-(6-(3-Propanoic acid, methyl ester)naphthyloxy)]-4-(3-pyridyl)-2-butanol A slurry of 10% palladium on charcoal (0.1 g) in ethyl acetate was added to a solution of (2R)-1-[2-(6-(3-trans-propenoic acid, methyl ester)naphthyloxy)]-4-(3-pyridyl)butan-2-ol (0.78 g, Example 2) in ethyl acetate:methanol (1:1) and hydrogenated for 5 hours at 3 atmospheres pressure. The reaction was filtered through celite® and the residue washed with methanol. The combined filtrate and washings were concentrated under reduced pressure to give the title compound as a cream solid (0.76 g).

m.p. 76–78° C.

MS (APCI) 380 (M+H)$^+$ $^1$H NMR (CDCl$_3$) 8.53(1H, d); 8.47(1H, dd); 7.67(2H, t); 7.57–7.55(2H, m); 7.30(1H, dd); 7.23–7.21(1H, m); 7.15–7.08(2H, m); 4.11–4.07(2H, m); 3.97–3.67(1H, m); 3.67(3H, s); 3.08(2H, t); 2.94–2.91(1H, m); 2.89–2.83(1H, m); 2.71(2H, t); 2.50(1H, br.s); 1.96–1.91(2H, m).

EXAMPLE 4

(2R)-1-[2-(6-(3-(N-Methyl)propanamide)naphthyloxy]-4-(3-pyridyl)-2-butanol (2R)-1-[2-(6-(3-Propanoic acid, methyl ester)naphthyloxy]-4-(3-pyridyl)-2-butanol (0.51 g, Example 3) was dissolved in methylamine (2.0 M solution in methanol, 20 ml) and heated at 100° C. in a pressure vessel for 16 hours. The residue was dissolved in dichloromethane to remove it from the vessel and then concentrated under reduced pressure. The residue was partitioned between ethyl acetate and ammonia. The organic layer was separated, washed with brine, dried over anhydrous magnesium sulfate, filtered and concentrated under reduced pressure. The residue was purified by column chromatography over silica eluting with ethyl acetate:methanol (19:1) to give an oil which was triturated with ether and filtered to give the title compound as a white solid (0.16 g).

m.p. 122–123° C.

MS (APCI) 379 (M+H)$^+$ $^1$H NMR (DMSO-D6) 8.47(1H, d); 8.40(1H, dd); 7.73–7.67(3H, m); 7.59(1H, s); 7.33–7.29(2H, m); 7.25(1H, d); 7.12(1H, dd); 5.08(1H, d); 3.98(2H, d); 3.97–3.83(1H, m); 2.92(2H, t); 2.89–2.65(2H, m); 2.55(3H, d); 2.49(2H, t); 1.90–1.73(2H, m).

EXAMPLE 5

(2R)-1-[2-(6-(3-trans-Propenoic acid)naphthyloxy)]-4-(3-pyridyl)-2-butanol

Water (5 ml) was added to a solution of (2R)-1-[2-(6-(3-trans-propenoic acid, methyl ester)naphthyloxy)]-4-(3-pyridyl)-2-butanol (0.90 g, Example 2) in tetrahydrofuran (10 ml) until the solution turned cloudy. Tetrahydrofuran was added dropwise until a clear solution reappeared and lithium hydroxide (0.20 g) was added. The solution was stirred at room temperature for 5 hours, then neutralised with aqueous hydrochloric acid (2M). The precipitate was collected by filtration, washed with water and dried under vacuum to give the title compound as a beige solid (0.65 g).

m.p. 199–201° C.

MS (APCI) 364 (M+H)$^+$ $^1$H NMR (DMSO-D6) 8.48(1H, d); 8.40(1H, d); 8.08(1H, s); 7.85(1H, d); 7.80(2H, s); 7.68(1H, d, J=15 Hz); 7.67(1H, s); 7.35–7.29(2H, m); 7.22(1H, dd); 6.59(1H, d, J=15 Hz); 4.02(2H, t); 3.88–3.83(1H, m); 3.40–3.20(1H, br.s); 2.85–2.68(2H, m); 1.93–1.72(2H, m).

EXAMPLE 6

(2R)-1-[2-(6-(3-(N-Methyl)propenamide)naphthyloxy]-4-(3-pyridyl)-2-butanol

A solution of trimethylaluminium (2.65 ml, 2.0M in toluene) was added dropwise to a suspension of methylamine hydrochloride (0.36 g) in dry toluene (6 ml) at 0° C. Once addition was complete, the reaction mixture was allowed to warm to room temperature and stirred for 1 hour. The resulting solution was then added to a solution of (2R)-1-[2-(6-(3-propenoic acid, methyl ester)naphthyloxy)]-4-(3-pyridyl)butan-2-ol (0.50 g, Example 2) in dry toluene (25 ml) and the resulting solution heated at reflux for 21 hours. After cooling, the reaction mixture was poured into water and acidified to pH 1 with aqueous hydrochloric acid (2M). The solution was basified using sodium hydrogen carbonate and extracted with ethyl acetate. The combined extracts were washed with brine, dried over anhydrous magnesium sulfate, filtered and concentrated under reduced pressure. The residue was purified by column chromatography over silica eluting with dichloromethane:methanol (19:1) to give the title compound as a yellow solid (0.09 g).

m.p. 133–134° C.

MS (APCI) 377 (M+H)$^+$ $^1$H NMR (DMSO-D6); 8.47(1H, d); 8.40(1H, dd); 8.05(1H, dd); 7.97(1H, s); 7.83(2H, t); 7.67(2H, m); 7.52(1H, d, J=15.5 Hz); 7.31(2H, m); 7.20(1H, d); 6.66(1H, d, J=15.5 Hz); 5.11(1H, d); 4.1(2H, d); 3.85(1H, m); 2.83–2.80(2H, m); 2.72(3H, d); 1.87–1.75(2H, m).

EXAMPLE 7

(2R)-1-[2-(6-(3-(N,N-Dimethyl)propenamide)naphthyloxy]-4-(3-pyridyl)-2-butanol.

Palladium (II) acetate (0.03 g), tri-o-tolylphosphine (0.08 g), N,N-dimethylacrylamide (1.39 ml) and triethylamine (2 ml) were added to a solution of (2R)-1-[2-(6-bromonaphthyloxy)]-4-(3-pyridyl)-2-butanol (0.50 g, Example 1) in acetonitrile (10 ml) and the mixture heated in a sealed tube at 70° C. for 16 hours. The solvents were removed under reduced pressure. The residue was purified by column chromatography over silica eluting with dichloromethane:methanol (19:1) to give the title compound as a beige solid (0.64 g).

m.p. 129–130° C.

MS (APCI) 391 [M+H]$^+$ $^1$H NMR (DMSO-D6) 8.48(1H,d); 8.41(1H,dd); 8.05(1H, s); 7.87–7.79(2H,m); 7.67(1H,d); 7.58(1H,d, J=15 Hz); 7.34–7.31(2H,m); 7.3 1(1H,d,J=15 Hz); 7.23–7.17(2H,m); 5.11 (1H,d); 4.02(2H,d); 3.86–3.83(1H,m); 3.19(3H,s); 2.94 (3H,s); 2.83–2.70(2H,m); 1.90–1.75(2H,m).

EXAMPLE 8

(2R)-1-[2-(6-(3-(N,N-Dimethyl)propanamide)naphthyloxy]-4-(3-pyridyl)-2-butanol.

A solution of (2R)-1-[2-(6-(3-(N,N-dimethyl)propenamide)naphthyloxy]-4-(3-pyridyl)-2-butanol (0.36 g, Example 7) in ethanol (150 ml) was hydrogenated for 43 hours at 3 atmospheres pressure using palladium on charcoal (10%, 0.036 g) as catalyst. The reaction was filtered through celite® and the residue washed with ethanol. The combined filtrate and washings were concentrated under reduced pressure and the residue purified by column chromatography over silica eluting with dichloromethane:methanol (19:1) to give the title compound as a brown solid (0.08 g).

m.p. 83–85° C.

MS (APCI) 393 (M+H)$^+$ $^1$H NMR (CDCl$_3$) 8.53(1H, dd); 8.48(1H, dd); 7.67(2H, t); 7.59–7.56(2H, m); 7.32(1H, dd); 7.26–7.21(1H, m); 7.15–7.09(2H, m); 4.11–4.07(2H, m); 4.0–3.97(1H, m); 3.10(2H, t); 2.96(3H, s); 2.93(3H, s); 2.91–2.80(2H, m); 2.71(2H, t); 2.41(1H, d); 1.99–1.91(2H, m).

EXAMPLE 9

(2R)-1-[2-(6-(3-Propanoic acid)naphthyloxy)]-4-(3-pyridyl)-2-butanol

Water (10 ml) was added to a solution of (2R)-1-[2-(6-(2-(propanoic acid, methyl ester)naphthyloxy)]-4-(3-pyridyl)-2-butanol (0.45 g, Example 3) intetrahydrofuran (20 ml) until the solution turned cloudy. Tetrahydrofuran was added dropwise until a clear solution reappeared and lithium hydroxide (0.10 g) was added. The solution was stirred at room temperature for 43 hours, then neutralised with aqueous hydrochloric acid (2M). The solution was concentrated under reduced pressure. The residue was triturated with ethanol and the solid filtered off. The filtrate was concentrated under reduced pressure to give a solid which was triturated with isohexane and filtered to give the title compound as a cream solid (0.32 g).

m.p. 225–226° C.

M.S. (APCI) 366 (M+H)$^+$ $^1$H NMR (DMSO-D6) 8.47(1H, d); 8.40(1H, dd); 7.68 (3H, t); 7.58(1H, s); 7.33–7.29(2H, m); 7.23(1H, d); 7.10 (1H, dd); 4.0(2H, d); 3.87–3.81(1H, m); 2.89(2H, t); 2.81–2.65(3H, m); 2.30(2H, t); 1.99–1.72(2H, m).

EXAMPLE 10

(2R)-1-[2-(6-(3-N-(Benzyloxycarbonylmethyl)propanamide)naphthyloxy]-4-(3-pyridyl)-2-butanol.

Glycine benzyl ester toluene-4-sulfonate (0.37 g), triethylamine (0.15 ml) and 1-hydroxybenzotriazole hydrate (0.148 g) were added to a solution of (2R)-1-[2-(6-(3-propanoic acid)naphthyloxy)]-4-(3-pyridyl)-2-butanol (0.40 g, Example 9) in dry N,N-dimethylformamide (30 ml) and the mixture stirred at room temperature under nitrogen for 20 minutes. 1-Ethyl-3-(3'-dimethylaminopropyl)carbodiimide hydrochloride (0.21 g) was added to the above solution and the mixture stirred at room temperature for 24 hours. The solution was concentrated under reduced pressure, the residue was dissolved in ethyl acetate, washed twice with brine, dried over anhydrous magnesium sulfate, filtered and concentrated under reduced pressure again. The residue was purified by column chromatography over silica eluting with dichloromethane:methanol (19:1) to give the title compound as a white solid (0.33 g).

m.p. 107–110° C.

MS (APCI) 513 [M+H]$^+$ $^1$H NMR (CDCl$_3$) 8.51(1H, d); 8.45(1H, dd); 7.64(2H, t); 7.58–7.55(2H, m); 7.39–7.20(7H, m); 7.12–7.07(2H, m); 6.05–6.02(1H, m); 5.15(2H, s); 4.05(4H, d); 3.99–3.93(1H, m); 3.09(2H, t); 2.97–2.76(3H, m); 2.60(2H, t); 1.98–1.80 (2H, m).

EXAMPLE 11
(2R)-1-[2-(6-(3-N-(Ethanoic acid)propanamide)naphthyloxy]-4-(3-pyridyl)-2-butanol.

A slurry of palladium on charcoal (10%, 0.02 g) in ethanol was added to a suspension of (2R)-1-[2-(6-(3-N-(benzyloxycarbonylmethyl)propanamide)naphthyloxy]-4-(3-pyridyl)-2-butanol (0.22 g, Example 10) in ethanol and hydrogenated for 5 hours at 1.5 atmospheres pressure. The reaction was filtered through celite® and the residue washed with ethanol The combined filtrate and washings were concentrated under reduced pressure to give the title compound as a beige solid (0.16 g).
m.p. 152–155° C.
MS (APCI) 423 [M+H]$^+$
$^1$H NMR (DMSO-D6) 8.46(1H, d); 8.40(1H, d); 8.13–8.09(1H, m); 7.74–7.62(4H, m); 7.34–7.30(2H, m); 7.25(1H, d); 7.12(1H, dd); 5.10(11H, m); 3.98(2H, d); 3.84–3.83(1H, m); 3.70(2H, d); 3.40(2H, t); 2.93(2H, t); 2.87–2.68(3H, m);1.90–1.69(2H, m).

EXAMPLE 12
(2R)-1-[2-(6-(3-(N-Acetylpiperazino)-1-oxopropyl)naphthyloxy]-4-(3-pyridyl)-2-butanol.

Prepared according to the method described in Example 10a)) from 1-acetyl piperazine (0.14 g), 1-hydroxybenzotriazole hydrate (0.149 g), (2R)-1-[2-(6-(3-propanoic acid)naphthyloxy)]-4-(3-pyridyl)-2-butanol (0.40 g, Example 9), dry N,N-dimethylformamide (30 ml) and 1-ethyl-3-(3'-dimethylaminopropyl)carbodiimide hydrochloride (0.21 g) to give the title compound as a white solid (0.6 g).
m.p. 39–41° C.
MS (APCI) 476 [M+H]$^+$
$^1$H NMR (CDCl$_3$) Two rotamers visible. 8.53(1H, d); 8.46(1H, dd); 7.69–7.64(2H, m); 7.58–7.56(2H, m); 7.31 (1H, dd); 7.26–7.21(1H, m); 7.13(1H, dd); 7.09–7.08(1H, m); 4.11–4.07(2H, m); 4.0–3.97(1H, m); 3.66–3.63(2H, m); 3.62–3.61(1H, m); 3.43–3.33(4H, m); 3.22–3.20(1H, m); 3.11(2H, t); 2.95–2.80(2H, m); 2.71(2H, t); 2.48(1H, d); 2.08(3H, s); 1.96–1.91(2H, m).

EXAMPLE 13
(2R)-1-[2-(6-(3(4-Morpholinyl)-1-oxopropyl)naphthyloxy]-4-(3-pyridyl)-2-butanol.

Prepared according to the method described in Example 10a) from morpholine (0.09 ml), 1-hydroxybenzotriazole hydrate (0.149 g), (2R)-1-[2-(6-(3-propanoic acid)naphthyloxy]-4-(3-pyridyl)-2-butanol (0.40 g, Example 9), dry N,N-dimethylformamide (30 ml) and 1-ethyl-3-(3'-dimethylaminopropyl)carbodiimide hydrochloride (0.21 g) to give the title compound as an amber oil (0.38 g).
MS (APCI) 435 [M+H ]+
$^1$H NMR (CDCl$_3$) 8.53(1H, d); 8.47(1H, dd); 7.67(2H, t); 7.58–7.56(2H, m); 7.31(1H, dd); 7.23–7.21(1H, m); 7.13(1H, dd); 7.10–7.09(1H, m); 4.10–4.07(2H, m); 4.0–3.97(1H, m); 3.61(4H, s); 3.48–3.45(2H, m); 3.37–3.34(2H, m); 3.11(2H, t); 2.94–2.78(2H, m); 2.68(2H, t); 2.46(1H, d); 1.99–1.91(2H, m).

EXAMPLE 14
(2R)-1-[2-(6-(3-N-(2-Hydroxyethyl)propanamide)naphthyloxy]-4-(3-pyridyl)-2-butanol.

Prepared according to the method described in Example 10a) from ethanolamine (0.066 ml), 1-hydroxybenzotriazole hydrate (0.149 g), (2R)-1-[2-(6-(3-propanoic acid)naphthyloxy)]-4-(3-pyridyl)-2-butanol (0.40 g, Example 9), dry N,N-dimethylformamide (30 ml) and 1-ethyl-3-(3'-dimethylaminopropyl)carbodiimide hydrochloride (0.21 g) to give the title compound as a white solid (0.35 g).
m.p. 93.5–96° C.
MS (APCI) 409 [M+H ]+
$^1$H NMR (DMSO-D6) 8.47(1H, d); 8.40(1H, dd); 7.84 (1H, t); 7.73–7.64(3H, m); 7.59(1H, s); 7.33–7.31(2H, m); 7.26(1H, d); 7.13(1H, dd); 5.09(1H, d); 4.63(1H, t); 3.98 (2H, d); 3.95–3.87(1H, m); 3.38–3.36(2H, m); 3.18–3.07 (2H, m); 2.95–2.89(2H, m); 2.85–2.65(2H, m); 2.47–2.41 (2H, t); 1.95–1.65(2H, m).

EXAMPLE 15
(2R)-1-[2-(6-(3-(4-(4-(1,1-Dimethylethoxycarbonyl))piperazine)-1-oxopropyl)naphthyloxy]-4-(3-pyridyl)-2-butanol.

Prepared according to the method described in Example 10a) from tert-butyl piperazine carboxylate (0.20 g), 1-hydroxybenzotriazole hydrate (0.149 g), (2R)-1-[2-(6-(3-propanoic acid)naphthyloxy)]-4-(3-pyridyl)-2-butanol (0.40 g, Example 9), dry N,N-dimethylformamide (30 ml) and 1-ethyl-3-(3'-dimethylaminopropyl)-carbodiimide hydrochloride (0.21 g) to give the title compound as a white solid (0.46 g).
m.p. 45–48° C.
MS (APCI) 434 [M—COO(CH$_3$)$_3$]$^+$
$^1$H NMR (CDCl$_3$) 8.53(1H, d); 8.47(1H, dd); 7.66(2H, t); 7.58–7.56(2H, m); 7.29(1H, dd); 7.22–7.21(1H, m); 7.13 (1H, dd); 7.09(1H, d); 4.10–4.07(2H, m); 4.03–3.98(1H, m); 3.59–3.57(2H, m); 3.38–3.33(4H, m); 3.28–3.26(2H, m); 3.11(2H, m); 2.95–2.78(2H, m); 2.69(2H, t); 2.58(1H, d); 1.99–1.90(2H, m); 1.47(9H, s).

EXAMPLE 16
(2R)-1-[2-(6-(3-(N-(Hexahydro-1,4-diazine)-1-oxopropyl)naphthyloxy]-4-(3-pyridyl)-2-butanol.

Trifluoroacetic acid (1 ml) was added to a solution of (2R)-1-[2-(6-(3-(4-(4-(1,1-dimethylethoxycarbonyl))piperazine)-1-oxopropyl)naphthyloxy]-4-(3-pyridyl)-2-butanol (0.31 g, Example 15) in dichloromethane (4 ml). The reaction was stirred at room temperature under nitrogen for 22 hours. The solution was neutralised by addition of saturated aqueous sodium hydrogencarbonate and extracted with dichloromethane. The combined extracts were dried over anhydrous magnesium sulfate, filtered and concentrated under reduced pressure. The residue was purified by column chromatography on silica eluting with dichloromethane:methanol (19:1) to give the title compound as a yellow oil (0.16 g).
MS (APCI) 434 [M+H]$^+$
$^1$H NMR (CDCl$_3$) 8.52(1H, d); 8.46(1H, dd); 7.66(2H, t); 7.58–7.56(2H, m); 7.32(1H, dd); 7.24–7.21(1H, m); 7.12 (1H, dd); 7.09(1H, s); 4.10–4.04(2H, m); 3.98–3.94(1H, m); 3.61(2H, t); 3.36(2H, t); 3.10(2H, t); 2.98–2.78(3H, m); 2.82(2H, t); 2.68(4H, t); 2.40–2.10(1H, br.s); 1.99–1.89(2H, m).

EXAMPLE 17
(2R)-1-[2-(6-(3-(N,N-Dimethyl)propanamide)naphthyloxy]-4-(3-pyridyl)-2-butanol.

(2R)-1-[2-(6-(3-(N,N-Dimethyl)propanamide)naphthyloxy]-4-(3-pyridyl)-2-butanol (0.05 g, Example 8) in dry tetrahydrofuran (15 ml) was added dropwise to borane in tetrahydrofuran (1.0M, 2.13 ml) under nitrogen at 0° C. The colourless solution was heated at reflux for 4 hours. After cooling, the solution was poured into aqueous hydrochloric acid (2M, 50 ml) then concentrated under reduced pressure. The residue was basified with sodium hydroxide pellets and extracted with ethyl acetate. The combined extracts were dried over anhydrous magnesium sulfate, filtered and concentrated under reduced pressure. The residue was purified by column chromatography on silica eluting with dichloromethane:methanol (99:1) to give a colourless oil (0.10 g).

MS (APCI) 379 [M+H]$^+$ $^1$H NMR (CDCl$_3$) 8.54(1H, d); 8.47(1H, dd); 7.82(1H, d); 7.69(2H, t); 7.56(1H, s); 7.46–7.42(1H, m); 7.30(1H, dd); 7.16–7.10(2H, m); 4.11–3.97(3H, m); 3.02–2.89(2H, m); 2.83–2.76(4H, m); 2.56(6H, s); 2.41(1H, d); 2.17–2.11(2H, m); 1.97–1.92(2H, m).

EXAMPLE 18
(2S)-1-[2-(6-Bromonaphthyloxy)]-4-(3-pyridyl)-2-butanol.

a) (2S, 3E/Z)-4-(3-Pyridyl)-1,2-O-isopropylidenebut-3-ene-1,2-diol

A solution of n-butyllithium (2.5 M in hexanes; 12 ml) was added dropwise to a stirred suspension of 3-pyridylmethyltriphenylphosphonium chloride hydrochloride (6.39 g, *J. Med. Chem.* 1986, 29, 1461) in tetrahydrofuran (50 ml) at −40° C. The resulting mixture was stirred at room temperature for 30 minutes and was then cooled to −70° C. A solution of 2,3-O-(R)-isopropylidene-D-glyceraldehyde (1.82 g) (ex Oxford Asymmetry; see *Organic Synthesis* (1995) 72, 6) in tetrahydrofuran (10 ml) was added. The resulting mixture was stirred and allowed to reach room temperature over 3 hours. The mixture was poured into brine (200 ml) and extracted into ethyl acetate. The combined extracts were dried over anhydrous magnesium sulfate, filtered and concentrated under reduced pressure. The residue was purified by column chromatography over silica eluting with diethyl ether to give the sub-title compound as an oil (2.24 g).

MS (EI) 205 (M)$^+$ $^1$H NMR (CDCl$_3$) major Z-diastereomer 8.53(2H, d); 7.61(1H, dt); 7.29(1H, dd); 6.67(1H, d); 5.85(1H, dd); 4.83(1H, q); 4.16(1H, t); 3.71(1H, t); 1.49(3H, s); 1.39(3H, s).

b) (2S)-4-(3-Pyridyl)-1,2-O-isopropylidenebutane-1,2-diol

The compound from Example 18a) (2.2 g) was dissolved in ethyl acetate (30 ml) and hydrogenated for 2 hours at 3 atmospheres pressure using 10% palladium on carbon (20 mg) as catalyst. The reaction was filtered through celite® and the residue washed with ethyl acetate. The combined filtrate and washings were concentrated under reduced pressure and the residue obtained purified by column chromatography over silica eluting with diethyl ether to give the sub-title compound as an oil (2.14 g).

MS (ESI) 208 (M+H)$^+$ $^1$H NMR (CDCl$_3$) 8.48–8.45(2H, m); 7.52(1H, dt); 7.23(1H, dd); 4.10(1H, quintet); 4.04(1H, t); 3.55(1H, t); 2.84–2.64(2H, m); 1.94–1.80(2H, m); 1.44(3H, s); 1.36(3H, s).

c) (2S)-4-(3-Pyridyl)-1,2-butanediol

The compound from Example 18b) (19.6 g) was dissolved in 2N hydrochloric acid (100 ml) and was stirred for 40 minutes. The mixture was neutralised with saturated aqueous sodium hydrogencarbonate solution and was concentrated under reduced pressure. The residue obtained was triturated with ethyl acetate and filtered. The residue was washed with ethyl acetate and the combined organic extracts were dried over anhydrous magnesium sulfate, filtered and concentrated under reduced pressure. The residue obtained was purified by column chromatography over silica eluting with ethyl acetate:methanol (9:1) to give the sub-title compound as an oil (13.21 g).

MS (APCI) 168 (M+H)$^+$ $^1$H NMR (CDCl$_3$) 8.44–8.40(2H, m); 7.54(1H, d); 7.22(1H, dd); 3.73–3.67(1H, m); 3.65(1H, dd); 3.48(1H, dd); 2.90–2.70(2H, bm); 2.87–2.68(2H, m); 1.84–1.67(2H, m).

d) (4S)-4-[2-(3-Pyridyl)ethyl]-1,3-dioxin-2-one

Prepared according to the method described in Example 1d) from a solution of (2S)-4-(3-pyridyl)-1,2-butanediol (11 g, Example 18c)) and 1,1'-carbonyldiimidazole (13 g) in chloroform (300 ml) to give the sub-title compound as an oil (7.3 g).

MS (APCI) 194 (M+H)$^+$ $^1$H NMR (CDCl$_3$) 8.50–8.45(2H, m); 7.55(1H, dt); 7.25(1H, dd); 4.70–4.65(1H, m); 4.55 (1H, t); 4.10 (1H, dd); 2.95–2.85 (1H, m); 2.80–2.70 (1H, m); 2.15–2.10 (1H, m); 2.05–1.95 (1H, m).

e) (2S)-1-[2-(6-Bromonaphthyloxy)]-4-(3-pyridyl)-2-butanol

Prepared according to the method described in Example 1e) from cesium carbonate (13.7 g), 6bromo-2-naphthol (9.27 g) and a solution of (4S)-4-[2-(3-pyridyl)ethyl]-1,3-dioxin-2-one (7.3 g, Example 18d)) in dry N,N-dimethylformamide (100 ml) to give the title compound as beige crystals after recrystallisation from aqueous ethanol (9.14 g).

m.p. 122–123° C.

MS (APCI) 372/4 (M+H)$^+$ $^1$H NMR (DMSO) 8.50(1H, d); 8.45(1H, dd); 8.10(1H, d); 7.75(2H, dd); 7.65(1H, dt); 7.55(1H, dd); 7.40–7.30(2H, m); 7.20(1H, dd); 5.10(1H, d); 4.00(2H, d); 3.90–3.85(1H, m); 2.90–2.70(2H, m); 1.90–1.75(2H, m).

EXAMPLE 19
(2S)-1-[2-(6-(3-(N,N-Dimethyl)propenamide)naphthyloxy]-4-(3-pyridyl)-2-butanol.

Prepared according to the method described in Example 7 from palladium (II) acetate (0.241 g), tri-o-tolylphosphine (0.654 g), N,N-dimethylacrylamide (1.1 ml), triethylamine (3 ml) and a solution of (2S)-1-[2-(6-bromonaphthyloxy)]-4-(3-pyridyl)butan-2-d (4 g, Example 18e)) in acetonitrile (9 ml) and to give the title compound as a white solid (3.13 g) after recrystallisation from aqueous ethanol.

m.p. 138–139° C.

MS (APCI) 391 [M+H]$^+$ $^1$H NMR (DMSO-D6) 8.50(1H, d); 8.40(1H, dd); 8.05 (1H, s); 7.90–7.80(3H, m); 7.65–7.70(1H, dt); 7.60(1H, d, J=18.36 Hz); 7.35–7.30(2H, m); 7.25(1H, d, J=18.36 Hz); 7.15(1H, dt); 5.10(1H, d); 4.05(2H, d); 3.90–3.85(1H, m); 3.20(3H, s); 2.95(3H, s); 2.90–2.65(2H, m); 2.0–1.70(2H, m).

EXAMPLE 20
(2S)-1-[2-(6-(3-(N,N-Dimethyl)propanamide)naphthyloxy]-4-(3-pyridyl)-2-butanol.

Prepared according to the method described in Example 8 from solution of (2S)-1-[2-(6-(3-(N,N-dimethyl)propenamide)naphthyloxy]-4-(3-pyridyl)-2-butanol (0.6 g, Example 17) in ethanol (150 ml) to give the title compound as a white solid (0.266 g) after trituration with ether:hexane (1:1).

m.p. 98–99° C.

MS (APCI) 393 (M+H)$^+$ $^1$H NMR (DMSO) 8.45(1H, s); 8.40(1H, d); 7.80–7.60 (4H, m); 7.40–7.30(2H, m); 7.25(1H, d); 7.15(1H, dt); 5.1(1H, d); 4.0(2H, d); 3.90–3.80(1H, m); 2.95–2.85(5H, m); 2.80(3H, s); 2.75–2.65(4H, m); 2.0–1.70(2H, m).

EXAMPLE 21
(2R)-1-[3'-(N,N-Dimethylphenylacetamide)-4-biphenyl-4-yloxy]-4-(3-pyridyl)-2-butanol, oxalic acid salt.

a) (2R)-1-(4-Bromophenoxy)-4-(3-pyridyl)butan-2-ol

The sub-titled compound was prepared by the method described in Example 1e) from cesium carbonate (8.1 g), 4-bromophenol (6.05 g) and a solution of (4R)-4-[2-(3-pyridyl)ethyl]-1,3-dioxin-2-one (4.8 g, Example 1d) in dry dimethylformamide (50 ml) to give (2R)-1-(4-bromophenoxy)-4-(3-pyridyl)-2-butanol as a beige solid (6.42 g).

m.p. 68–69° C.

MS (APCI) 322/324 (M+H)$^+$ $^1$H NMR (CDCl$_3$) 8.50(1H, d); 8.45(1H, dd); 7.55(1H, dt); 7.35(2H, d); 7.25–7.20(1H, m); 6.80–6.75(2H, m); 4.10–3.90(2H, m); 3.85(1H, dd); 2.95–2.90(1H, m); 2.85–2.75(1H, m); 2.65(1H, s); 1.90–1.80(2H, m).

b) (2R)-1-(4-Bromophenoxy)-4-(3-pyridyl)-2-(tert-butyldimethylsilyloxy)butane tert-Butyldimethylsilylchloride (3.75 g) and imidazole (1.69 g) were added to a solution of (2R)-1-(4-bromophenoxy)-4-(3-pyridyl)-2-butanol (4 g, Example 21a)) in dichloromethane. The mixture was stirred for 16 hours at room temperature. The white precipitate was collected by filtration and the filtrate concentrated under reduced pressure to give the sub-title compound as an oil (5.4 g)

MS (APCI) 436/438 (M+H)$^+$ $^1$H NMR (CDCl$_3$) 8.50(1H, d); 8.45(1H, dd); 7.55(1H, dt); 7.35(2H, d); 7.25–7.20(1H, m); 6.80–6.75(2H, dd); 4.15–4.05(1H, m); 3.90–3.75(2H, m); 2.95–2.80(2H, m); 2.0–1.90(2H, m), 0.95–0.9(9H, m); 0.15–0.10(6H, m).

c) (2R)-4-[4-(3-Pyridyl)-2-(tert-butyldimethylsilyloxy)butoxy]benzeneboronic acid A solution of n-butyllithium (2.5 M in hexanes, 6.9 ml, CAUTION) was added dropwise to a stirring solution of (2R)-1-(4-bromophenoxy)-4-(3-pyridyl)-2-(tert-butyldimethylsilyloxy)butane (1.50 g, Example 21b)) and triisopropyl borate (4.3 ml) in tetrahydrofuran (200 ml) at −70° C. After the addition was complete the reaction mixture was allowed to warm to room temperature. After 1 hour water (200 ml) and ethyl acetate (200 ml) were added. The organic phase was separated, dried over anhydrous magnesium sulfate, filtered and concentrated under reduced pressure to give an oil. This was partly purified by column chromatography over silica eluting with dichloromethane then ethyl acetate then methanol to give the sub-title compound as a glass (2 g).

MS (APCI) 402 (M+H)$^+$ $^1$H NMR (CDCl$_3$) 8.60(1H, d); 8.55(1H, dd); 7.95(2H, d); 7.60(1H, d); 7.30 (1H, dd); 6.90(2H, d ); 4.15–4.05(1H, m); 3.95–3.80(2H, m); 2.95–2.70(2H, m); 2.05–1.80(2H, m); 0.95–0.9(9H, m); 0.15–0.10(6H, m).

d) (2R)-1-[3'-(N,N-Dimethylphenylacetamide)-4-biphenyl-4-yloxy]-4-(3-pyridyl)-2-butanol Prepared according to the method described by Suzuki et al. (Syn. Comm. 1981, 11, 513–519) from toluene (7 ml), aqueous sodium carbonate (2 M, 1.0 ml), ethanol (2 ml), 3-bromophenylacetamide (0.365 g), (2R)-4-[4-(3-pyridyl)2-(tert-butyldimethylsilyloxy)-butoxy]benzeneboronic acid (0.4 g, Example 21c)) and tetrakis(triphenylphosphine)-palladium(0) (0.1 g) with heating at 100° C. for 16 hours. The solution was then poured into water and twice extracted with ethyl acetate. The combined extracts were dried over anhydrous magnesium sulfate, filtered and concentrated under reduced pressure to give an oil.

This residue was treated with aqueous hydrochloric acid (2M, 2 ml) in methanol (10 ml) for 20 hours. The residue obtained after evaporation was treated with aqueous hydrochloric acid (2M, 20 ml) and extracted twice with ethyl acetate. These extracts were discarded, the aqueous solution basified with aqueous sodium hydrogen carbonate and the solution extracted twice with ethyl acetate. The combined extracts were dried over anhydrous magnesium sulfate, filtered and concentrated under reduced pressure to give an oil which was purified by column chromatography over silica eluting with dichloromethane:methanol (10:1). Treatment of the sub-title compound with a saturated ethereal solution of oxalic acid generated the oxalate salt as a white foam (0.154 g).

MS (APCI) 405 (M (-oxalic acid)+H)$^+$ $^1$H NMR (DMSO) 8.50(1H, s); 8.45(1H, d); 7.70–7.65 (1H, m); 7.55(2H, d); 7.45(2H, d); 7.35–7.30(2H, m); 7.15 (1H; d); 7.05(2H, d); 3.90(2H, d); 3.85–3.75(1H, m); 3.70 (2H, s); 3.0(3H, s); 2.90–2.65(5H, m); 1.95–1.65(2H, m).

EXAMPLE 22

(2R)1-[2-(6-(3-(N-6-(1,1-Dimethylethylcarbamoyl)hexyl) propanamide)naphthyl-oxy]-4-(3-pyridyl)-2-butanol.

Prepared according to the method described in Example 10, from N-boc-1,6-diamino-hexane hydrochloride (0.202 g), 1-hydroxybenzotriazole hydrate (0.065 g), triethylamine (0.11 ml), (2R)-1-[2-(6-(3-propanoic acid)naphthyloxy]-4-(3-pyridyl)-2-butanol (0.147 g, Example 9), dry N,N-dimethylformamide (20 ml) and 1-ethyl-3-(3'-dimethylaminopropyl)carbodiimide hydrochloride (0.092 g) to give the title compound as a pale yellow solid (0.116 g).

m.p. 114–115° C.

MS (APCI) 464 [M+H]$^+$ $^1$H NMR (DMSO-D6) 8.47(1H, d); 8.39(1H, dd); 7.76 (1H, t); 7.72–7.64(3H, m); 7.58(1H, s); 7.32–7.29(2H, m); 7.25(1H, d); 7.13(1H, dd); 6.74(1H, t); 5.08(1H, d); 3.98 (2H, d); 3.83(1H, q); 3.02–2.71(8H, m); 2.42(2H, t); 2.96–2.68(2H, m); 1.63(9H, s); 1.3(4H, t); 1.15(4H, bs).

Pharmacological Activity

The pharmacological activity of the compounds of the invention may be tested by the method of E. Wells et al, 'Characterization of primate bronchoalveolar mast cells: II—inhibition of histamine, LTC$_4$ and PGD$_2$ release from primate bronchoalveolar mast cells and a comparison with rat peritoneal mast cells', J. Immunol., vol. 137, 3941, 1986.

The compounds of examples 1 to 22 were tested and found to inhibit histamine release at a concentration of less than 10$^{-5}$ M (IC$_{50}$).

What is claimed is:

1. A compound of formula I:

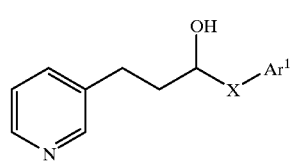

(I)

wherein;

X is (CH$_2$)$_n$O, (CH$_2$)$_n$S or CH$_2$CH$_2$;

n is 1 or 2;

Ar$^1$ is naphthyl or biphenyl substituted by one or more groups selected from —Y—NR$^1$C(O)NR$^2$R$^3$, —Y—C(O)NR$^2$R$^3$, Y—C(O)OR$^4$, Y—Z—NR$^2$R$^3$, —Y—NR$^5$C(O)NR$^6$—Z—R$^7$; and —Y—C(O)NR$^6$—Z—R$^7$; where:

Y is CH=CH or CH$_2$CH$_2$;

R$^2$ and R$^3$ are independently hydrogen or C$_{1-6}$ alkyl or together with the nitrogen atom to which they are attached form an optionally substituted 5- to 7-membered heterocyclic ring optionally containing a further heteroatom selected from nitrogen, oxygen or sulfur;

R¹, R⁵ and R⁶ are independently hydrogen or $C_{1-10}$ alkyl (optionally substituted by one or more fluorine atoms);

R⁴ is hydrogen or $C_{1-4}$ alkyl;

Z is $C_{1-6}$ alkylene; and

R⁷ is a group $NR^5C(O)R^6$, $NR^5CO_2R^6$, $NR^2R^3$, $CO_2R^8$ or $OR^9$, where $R^2$, $R^3$, $R^5$ and $R^6$ are as defined above, $R^8$ is hydrogen, $C_{1-6}$ alkyl, $C_{1-6}$ alkylaryl or aryl optionally substituted by hydroxy, and $R^9$ is hydrogen or $C_{1-6}$ alkyl, or a salt or solvate thereof.

2. A compound according to claim 1 in which X is $CH_2O$, $CH_2S$ or $CH_2CH_2$.

3. A compound according to claim 1 which is;
(2R)-1-[2-(6-(3-trans-Propenoic acid, methyl ester)naphthyloxy)]-4-(3-pyridyl)-2-butanol,
(2R)-1-[2-(6-(3-Propanoic acid, methyl ester)naphthyloxy)]-4-(3-pyridyl)-2-butanol,
(2R)-1-[2-(6-(3-(N-methyl)propanamide)naphthyloxy]-4-(3-pyridyl)-2-butanol,
(2R)-1-[2-(6-(3-trans-Propenoic acid)naphthyloxy)] -4-(3-pyridyl)-2-butanol,
(2R)-1-[2-(6-(3-(N-methyl)propenamide)naphthyloxy]-4-(3-pyridyl)-2-butanol,
(2R)-1-[2-(6-(3-(N,N-Dimethyl)propenamide)naphthyloxy]-4-(3-pyridyl)-2-butanol,
(2R)-1-[2-(6-(3-(N,N-Dimethyl)propanamide)naphthyloxy]-4-(3-pyridyl)-2-butanol,
(2R)-1-[2-(6-(3-propanoic acid)naphthyloxy)]-4-(3-pyridyl)-2-butanol,
(2R)-1-[2-(6-(3-N-(benzyloxycarbonylmethyl)propanamide)naphthyloxy]-4-(3-pyridyl)-2-butanol,
(2R)-1-[2-(6-(3-N-(Ethanoic acid)propanamide)naphthyloxy]-4-(3-pyridyl)-2-butanol,
(2R)-1-[2-(6-(3-(N-Acetylpiperazino)-1-oxopropyl)naphthyloxy]-4-(3-pyridyl)-2-butanol,
(2R)-1-[2-(6-(3-(4-Morpholinyl)-1-oxopropyl)naphthyloxy]-4-(3-pyridyl)-2-butanol,
(2R)-1-[2-(6-(3-N-(2-Hydroxyethyl)propanamide)naphthyloxy]-4-(3-pyridyl)-2-butanol,
(2R)-1-[2-(6-(3-(4-(4-(1,1-Dimethylethoxycarbonyl))piperazine)-1-oxopropyl)naphthyloxy]-4-(3-pyridyl)-2-butanol,
(2R)-1-[2-(6-(3-(N-(Hexahydro-1,4-diazine)-1-oxopropyl)naphthyloxy]-4-(3-pyridyl)-2-butanol,
(2R)-1-[2-(6-(3-(N,N-Dimethyl)propanamide)naphthyloxy]-4-(3-pyridyl)-2-butanol,
(2S)-1-[2-(6-(3-(N,N-Dimethyl)propenamide)naphthyloxy]-4-(3-pyridyl)-2-butanol,
(2S)-1-[2-(6-(3-(N,N-Dimethyl)propanamide)naphthyloxy]-4-(3-pyridyl)-2-butanol,
(2R)-1-[3'-(N,N-Dimethylphenylacetamide)-4-biphenyl-4-yloxy]-4-(3-pyridyl)-2-butanol,
(2R)-1-[2-(6-(3-(N-6-(1,1-Dimethylethylcarbamoyl)hexyl)propanamide)naphthyl-oxy]-4-(3-pyridyl)-2-butanol,
or a salt or solvate thereof.

4. A pharmaceutical composition comprising a compound of formula I or a salt or solvate thereof as defined in claim 1 in association with a pharmaceutically acceptable adjuvant, diluent or carrier.

5. A method of treating asthma comprising administering to a patient in need of such treatment an effective amount of a compound of formula (I) in claim 1.

* * * * *